United States Patent
Torgerson

(10) Patent No.: US 11,458,303 B2
(45) Date of Patent: Oct. 4, 2022

(54) IMPLANTABLE MEDICAL LEADS HAVING FEWER CONDUCTORS THAN DISTAL ELECTRODES

(71) Applicant: MEDTRONIC, INC., Minneapolis, MN (US)

(72) Inventor: Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 319 days.

(21) Appl. No.: 16/384,746

(22) Filed: Apr. 15, 2019

(65) Prior Publication Data

US 2020/0324109 A1 Oct. 15, 2020

(51) Int. Cl.
*A61N 1/05* (2006.01)
*A61N 1/36* (2006.01)

(52) U.S. Cl.
CPC ......... *A61N 1/0551* (2013.01); *A61N 1/0502* (2013.01); *A61N 1/36062* (2017.08)

(58) Field of Classification Search
CPC .... A61N 1/048; A61N 1/0488; A61N 1/0502; A61N 1/0551; A61N 1/0553; A61N 1/36062
USPC ...................................... 607/46, 72
See application file for complete search history.

(56) References Cited

U.S. PATENT DOCUMENTS

| | | | |
|---|---|---|---|
| 5,325,870 A | 7/1994 | Kroll | |
| 5,531,782 A | 7/1996 | Kroll | |
| 6,327,498 B1 | 12/2001 | Kroll | |
| 7,676,275 B1 | 3/2010 | Farazi et al. | |
| 8,055,351 B2 | 11/2011 | Atalar | |
| 8,180,456 B2 | 5/2012 | Pontiga | |
| 8,744,548 B2 * | 6/2014 | Receveur | A61N 1/056 600/373 |
| 8,798,768 B2 | 8/2014 | Kaula et al. | |
| 9,242,090 B2 | 1/2016 | Atalar | |
| 9,409,023 B2 * | 8/2016 | Burdick | A61N 1/36003 |
| 9,604,048 B2 | 3/2017 | Govea | |
| 10,716,942 B2 * | 7/2020 | Zhang | A61N 1/36185 |
| 2013/0023950 A1 * | 1/2013 | Gauthier | A61N 1/37247 607/46 |

(Continued)

*Primary Examiner* — Carl H Layno
*Assistant Examiner* — Jane C Kalinock
(74) *Attorney, Agent, or Firm* — Withers & Keys, LLC

(57) ABSTRACT

Implantable medical systems include implantable percutaneous medical leads and/or implantable medical lead extensions that have fewer conductors than distal electrodes, or distal connectors for extensions, by having one or more conductors be electrically coupled to multiple distal electrodes. The multiple distal electrodes may span a general area of a body of a patient that includes a specific point that requires therapy, such as multiple vertebral segments. Because all distal electrodes spanning the general area that are coupled to an active conductor will output the stimulation therapy, the specific point within the general area will receive the therapy even without identifying which electrode is most effective. Bipolar and unipolar stimulation modes may be used. Multiple leads may be used where each lead has more distal electrodes than conductors. Additionally, a single lead may have more distal electrodes than conductors while also carrying multiple stimulation waveforms.

17 Claims, 9 Drawing Sheets

(56) References Cited

U.S. PATENT DOCUMENTS

2017/0281949 A1* 10/2017 Thacker .............. A61N 1/36071
2018/0126152 A1* 5/2018 Leven .................. A61N 1/0551

* cited by examiner

IMPLANTABLE MEDICAL LEADS HAVING FEWER CONDUCTORS THAN DISTAL ELECTRODES

TECHNICAL FIELD

Embodiments include implantable percutaneous leads or lead extensions that include fewer conductors that carry signals to the distal electrodes than the number of distal electrodes that are present.

BACKGROUND

Medical devices that provide stimulation therapy via a percutaneously implanted lead conventionally include a device that contains a stimulation engine that produces stimulation pulses. The implanted percutaneous lead conventionally includes electrical conductors contained within a lead body where distal electrodes are located on a distal end of the lead. Each electrical conductor has a corresponding distal electrode. The stimulation engine thereby outputs a signal for each distal electrode.

In some cases, the stimulation therapy being provided can be focused into a small area that may be provided by a single pairing of anode and cathode electrodes providing bipolar stimulation or by a single electrode providing unipolar stimulation. However, it may be difficult to implant the lead so that a specific electrode is present at precisely the correct location. For instance, the general area where the stimulation is required, such as an area spanning multiple vertebral segments in the case of spinal cord stimulation, may be known but the precise location where stimulation is needed within the general area may not be known. To address this issue, the lead has more electrodes and associated conductors than are actually needed to stimulate the specific location. The lead is implanted so that the electrodes span the general area where stimulation is needed, and each electrode pairing is tested to find the electrode pairing that best stimulates the specific area that needs the stimulation.

While this approach is satisfactory for achieving stimulation therapy, the lead construction is complex due to the number of conductors that are present. Furthermore, the number of conductors within the lead adds to the bulk and cost of the lead and limits the amount of electrodes that can be used for therapy if each electrode needs an independent conductor through the lead body to the stimulation device.

SUMMARY

Embodiments address issues such as these and others by providing percutaneous leads or lead extensions such as those used for spinal cord stimulation therapy and other types of stimulation therapy that include more distal electrodes than conductors that deliver signals to the distal electrodes. Thus, multiple distal electrode pairings that allow the specific target site within the general area to be reached are still provided, but the number of conductors within the percutaneous lead or lead extension is smaller because a single conductor is electrically coupled to multiple distal electrodes.

Embodiments provide an implantable percutaneous medical lead that includes a percutaneous lead body having a proximal area configured to be mechanically coupled to a medical device and a first proximal contact coupled to the proximal area of the percutaneous lead body. The implantable medical lead includes a first plurality of distal ring electrodes being spaced apart along an axial dimension of the percutaneous lead body and coupled to a distal area of the percutaneous lead body to configure the implantable percutaneous medical lead for stimulation, such as spinal cord stimulation across multiple vertebral segments. The implantable percutaneous medical lead also includes a first conductor electrically coupled to the first proximal contact, extending through the percutaneous lead body, and electrically coupled to the plurality of distal ring electrodes.

Embodiments provide an implantable medical system that includes a medical device that has a stimulation engine. The implantable medical system also includes a first implantable percutaneous medical lead. The first implantable medical lead includes a percutaneous lead body that is mechanically coupled to the medical device and includes a plurality of distal ring electrodes being spaced from apart along an axial dimension of the percutaneous lead body and coupled to a distal area of the percutaneous lead body to configure the implantable percutaneous medical lead for stimulation, such as spinal cord stimulation across multiple vertebral segments. The first implantable medical lead also includes a first conductor electrically coupled to the stimulation engine, extending through the percutaneous lead body, and electrically coupled to the plurality of distal ring electrodes.

Embodiments provide a method of providing electrical stimulation, such as spinal cord stimulation across multiple vertebral segments. The method involves generating an electrical stimulation pulse at a stimulation engine of a medical device and carrying the electrical stimulation pulse through a first electrical conductor within an implantable percutaneous medical lead that is mechanically coupled to the medical device. The method further involves providing the electrical stimulation pulse at a first plurality of distal ring electrodes of the implantable percutaneous medical lead that are electrically coupled to the first electrical conductor where the first plurality of distal ring electrodes span the multiple vertebral segments.

DETAILED DESCRIPTION

Embodiments provide percutaneous leads or lead extensions that include fewer conductors than distal electrodes, and/or distal connectors of lead extensions, by coupling multiple distal electrodes and/or distal connectors to a same conductor. The stimulation pulses are provided across all the electrodes to span the general area of therapy. In this manner, the target site within the general area of therapy receives the stimulation therapy even though a minimal number of conductors may be present within the percutaneous lead and/or lead extension.

Figure 1:
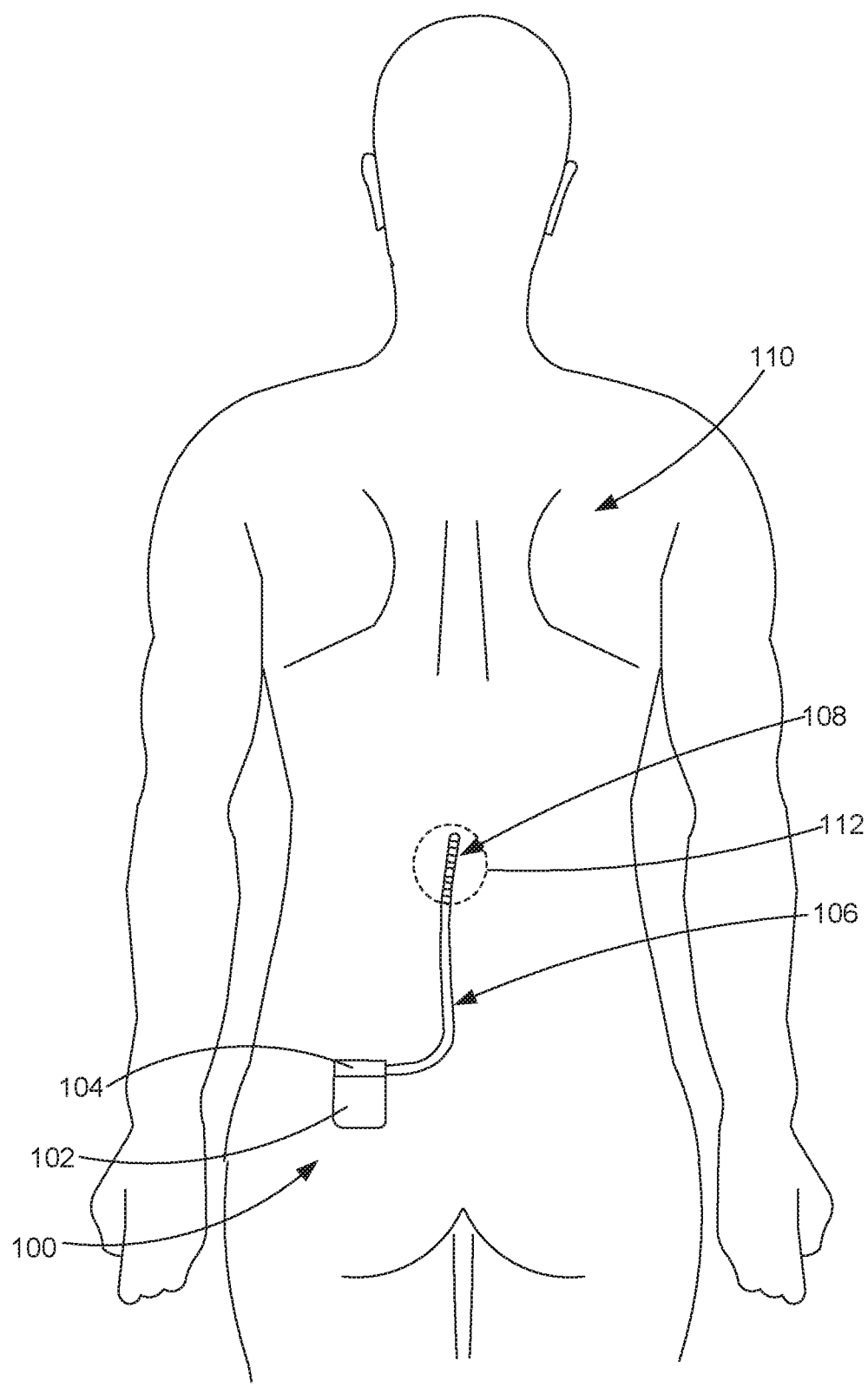
FIG. 1 shows an example of an environment for use of various embodiments of implantable percutaneous medical leads or extensions where there are fewer conductors than distal electrodes.

FIG. 1 shows an example of an environment where implantable medical systems that include embodiments of such percutaneous leads or lead extensions may be used. In this example, an implantable medical system 100 has been implanted within a patient 110. The implantable medical system includes a medical device 102 that is capable of generating stimulation pulses to provide stimulation therapy to the patient 110. The medical device 102 may be implanted or may be externally mounted to the patient, such as for therapy trial periods. The medical device of this example 102 includes a header 104 that receives the proximal end of an implantable medical lead 106 or an implantable lead extension.

The implantable percutaneous medical lead 106 is routed from the medical device 102, or from a distal of a lead extension when present, so that a distal end of the lead 106 is present within a general therapy area 112 within the patient 110. The lead 106 includes a set of axially spaced distal electrodes 108 in the form of rings that either fully or partially surround a body of the lead 106. The set of distal electrodes 108 may be used to provide bipolar stimulation where one more electrodes of the set 108 act as a cathode while one or more other electrodes of the set 108 act as an anode. Alternatively, the set of distal electrodes 108 may be used to provide unipolar stimulation where all or a subset of the electrodes of the set 108 provide one node and the housing of the medical device 102 provides the other node of the stimulation circuit.

The implantable medical lead 106 may be implanted percutaneously by being inserted through a needle into the region of the stimulation area 112, such as within the epidural space. Thus, the diameter of the implantable percutaneous medical lead 106 including the distal end where the electrodes 108 are located is configured to fit within a lumen of a corresponding insertion needle. For instance, in a non-limiting specific example, the percutaneous medical lead 106 may have a lead body and electrode ring diameter in the range of 0.040 to 0.060 inch via an insertion needle having a gauge of 14. Other lead and ring diameters with insertion needles of a different gauge are also applicable.

In this example, the medical device 102 is a neurostimulator providing spinal cord stimulation in the area 112 of the spinal cord where area 112 spans multiple vertebral segments, such as multiple cervical segments, multiple thoracic segments, and/or multiple lumbar segments. However, there are many other examples where the embodiments described herein are also applicable, such as where the area 112 is in proximity to a peripheral nerve to be stimulated, an area under the skin in an area of pain commonly referred to as peripheral nerve field stimulation, a nerve related to incontinence, or a deep brain stimulation site.

FIGS. 2A-2D show various illustrative configurations of the implantable medical systems and specifically the configuration of the medical device 102 and the proximal end of one or more percutaneous leads 106 or lead extensions. Corresponding distal ends of the percutaneous leads 106 are shown in FIGS. 3A-3D and are described in more detail below. Lead extensions are show in more detail in FIGS. 4A and 4B and are also described in more detail below.

Figure 2A:
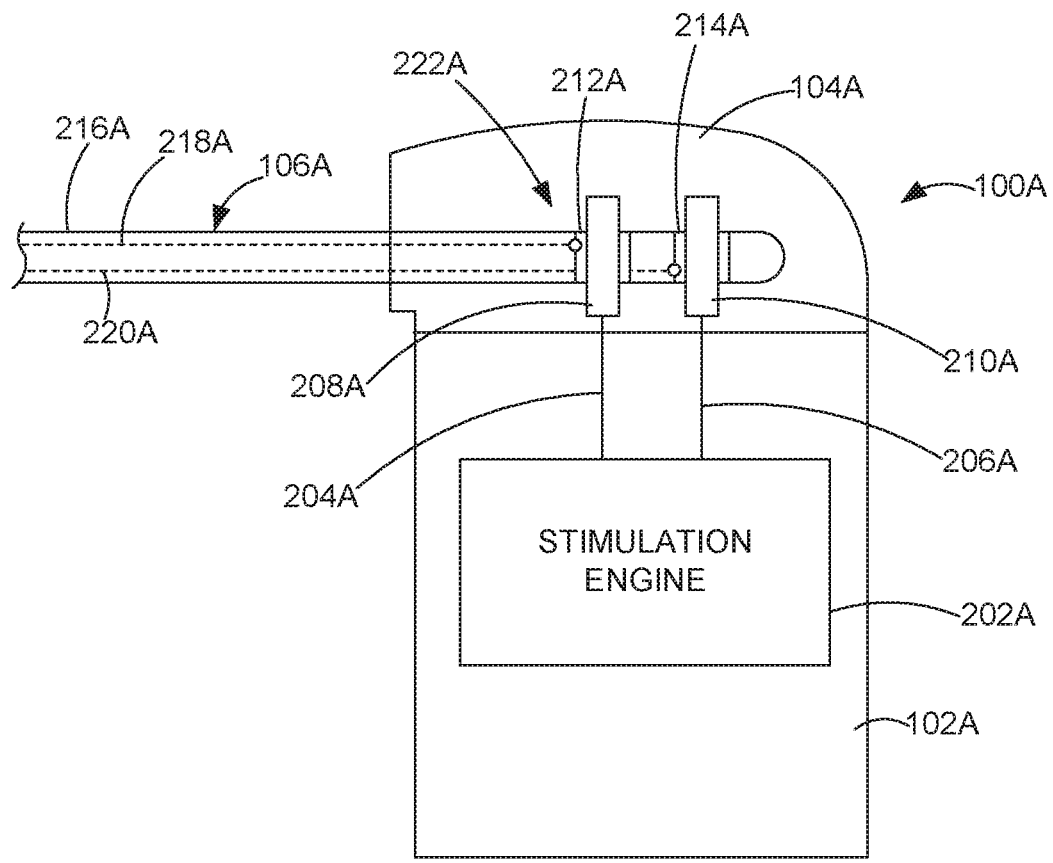
FIG. 2A shows an example of an implantable medical system that includes a medical device coupled to a first embodiment of an implantable percutaneous medical lead.

FIG. 2A shows a configuration of an implantable medical system 100A where medical device 102A includes a stimulation engine 202A that generates the stimulation pulses. In this example, the stimulation engine 202A is configured for bipolar stimulation of a single output pair by outputting stimulation pulses across header connectors 208A and 210A within the header 104A, such as where connector 208A as a pulse delivery connector while connector 210A is a pulse return connector. Device conductors 204A and 206A, such as lead frame conductors, feedthrough pins, and combinations thereof, carry the stimulation pulse signal between the stimulation engine 202A and the connectors 208A and 210A by transitioning into the header 104A. While FIG. 2A shows a single output pair via the pairing of device conductors 204A and 206A that are being used for the stimulation therapy, the stimulation engine 202A may have additional stimulation outputs although they may remain inactive.

A proximal end 222A of the lead 106A is configured to be mechanically coupled to the medical device 102A where it is present and affixed within a lead bore of the header 104A where the connectors 208A and 210A are present. The lead is affixed in such a way as to be removable from the mechanical coupling, such as by using a set screw or other fixation mechanism that can release the lead 106A to provide the mechanical coupling. The proximal end 222A includes proximal contacts 212A and 214A that electrically couple to the connectors 208A and 210A, respectively. One conductor carries the stimulation pulses of the stimulation waveform to the target and the other returns the stimulation pulses back to the stimulation engine 202A to complete the circuit in a bipolar configuration. Conductors 218A and 220A are shown in phantom for purposes of illustration as they are contained within the non-conductive lead body 216A and are electrically coupled to the proximal contacts 212A and 214A, respectively. While the conductors 218A and 220A are shown as being linear, it will be appreciated that these conductors 218A and 220A may instead be coiled. In either case, the conductors 218A and 220A are electrically isolated from one another such as via a non-conductive jacket and/or coating about each conductor.

Because the lead 106A includes only two conductors 218A and 220A even though there are more than two distal electrodes, the amount of space required for the set of conductors is less than for a lead that utilizes a separate conductor for each distal electrode. Therefore, the lead body 216A may be made smaller than would be typical, or alternatively, the conductors 218A and 220A may be made with a thicker filar than would be typical. For example, the conductors 218A and 220A may each have a thickness of greater than 0.004 inch for a lead body diameter of 0.052 inch or less. Additionally, where the conductors 218A and 220A are coiled, the pitch may be tighter than would be typical for a lead with a separate conductor for each distal electrode. Furthermore, rather than reducing the diameter of the lead body, the number of distal electrodes may be increased, such as having 16 or more electrodes in a lead body carrying four conductors. Additionally, for leads that utilize cable conductors instead of coils and do not require a stylet lumen, the lead diameter may be reduced substantially.

As discussed in more detail below with reference to FIGS. 3A and 3B, the distal end of the lead 106A may include several electrodes even though there are only two conductors 218A and 220A carrying the stimulation signal to the distal end of the lead 106A. One or both conductors 218A and 220A may be electrically coupled to multiple distal electrodes, where one conductor such as conductor 218A is a stimulation conductor providing the delivery path while the other conductor 220A is a stimulation conductor providing the return path.

The consequence of this configuration of multiple electrodes per conductor 218A, 220A is that stimulation is being provided across the entire region 112 that the distal electrodes span, as opposed to being provided only at a single target point within the region 112. The effect may be that a larger area of paresthesia is produced for the patient 110 where the stimulation pulse frequency is in the typical range of tens or hundreds of Hertz. However, this paresthesia may be alleviated by utilizing alternative forms of stimulation therapy, such as where the stimulation pulse frequency is much higher, in the hundreds of kilohertz, such as in the range of 400-600 kHz, for example.

Figure 2B:
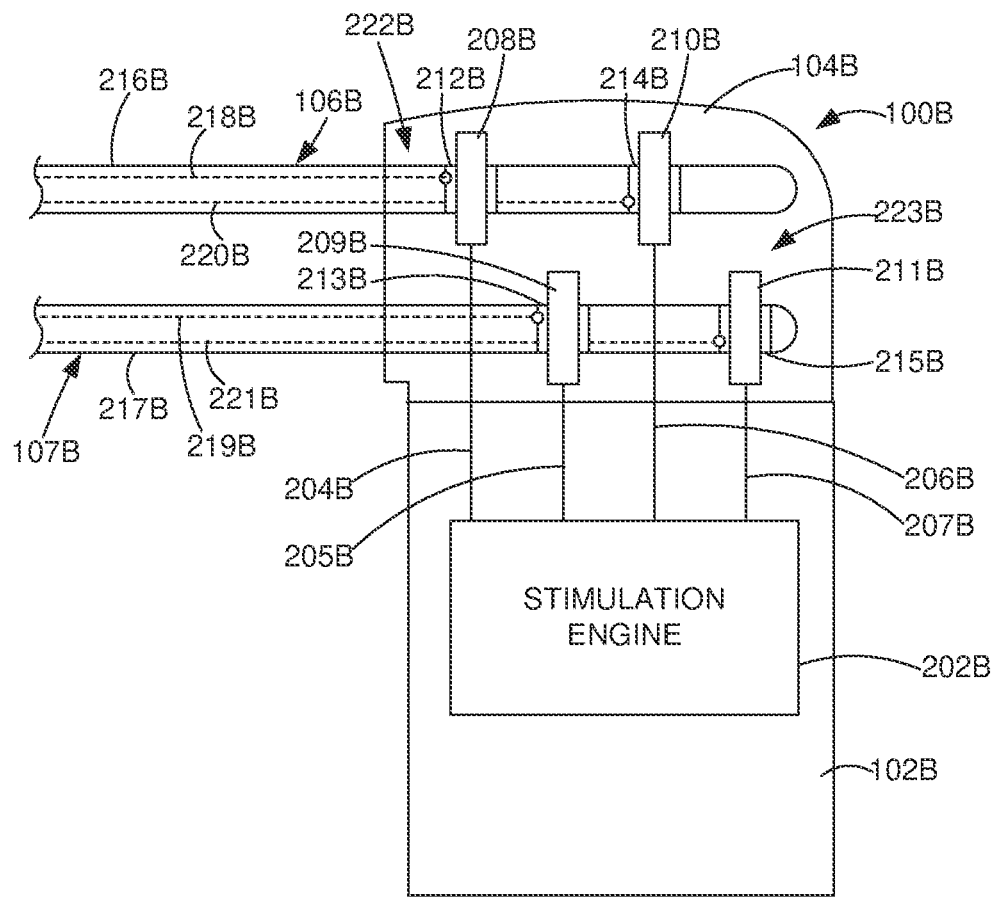
FIG. 2B shows a second example of an implantable medical system that includes a medical device coupled to multiple implantable percutaneous medical lead embodiments.

FIG. 2B shows a configuration of an implantable medical system 100B where medical device 102B includes a stimulation engine 202B that generates the stimulation pulse waveforms for two leads 106B and 107B. In this example, the stimulation engine 202B is configured for bipolar stimulation of two output pairs, one per lead, by outputting stimulation pulses across header connectors 208B and 210B and across header connectors 209B, 211B within the header 104B. The stimulation engine may produce identical stimulation pulses simultaneously so that both leads 106B and 107B produce identical simultaneous outputs within the area to be stimulated. Connectors 208B and 209B act as pulse delivery connectors while connectors 210B and 211B are pulse return connectors. Device conductors 204B, 205B, 206B, and 207B, such as lead frame conductors, feedthrough pins, and combinations thereof, carry the stimulation pulse signals between the stimulation engine 202B and the connectors 208B, 209B, 210B, and 211B by transitioning into the header 104B.

When providing stimulation therapy via multiple leads such as the two leads 106B and 107B, the stimulation engine 202B may be configured in various ways. For instance, in some cases such as where the two leads are stimulating different areas requiring therapy, it may be beneficial to have two different stimulation waveforms, one per lead, where the pulses of the waveforms may differ in amplitude, duration, or frequency. Thus, the stimulation engine 202B is configured to produce one waveform across one output pair 204B, 206B while being configured to produce a different waveform across another output pair 205B, 207B, interleaving the pulses in time to keep the therapy pulses from lead 106B from interacting with the pulses from lead 107B. Alternatively, such as where the same therapy area is being stimulation by multiple leads such as the two leads 106B and 107B, it may be beneficial to produce identical waveforms at both leads 106B, 107B. Thus, the stimulation engine 202B is configured to produce one waveform across one output pair 204B, 206B while being configured to produce an identical waveform across another output pair 205B, 207B. While FIG. 2B shows the two output pairs via the pairing of device conductors 204B and 206B as one pair and 205B and 207B as another that are being used for the stimulation therapy, the stimulation engine 202B may have additional stimulation outputs although they may remain inactive.

Like the lead 106A of FIG. 2A, a proximal end 222B of the lead 106B is configured to be mechanically coupled to the medical device 102B where it is present and affixed within a lead bore of the header 104B where the connectors 208B and 210B are present. The proximal end 222B includes proximal contacts 212B and 214B that electrically couple to the connectors 208B and 210B, respectively. Conductors 218B and 220B shown in phantom for purposes of illustration as they are contained within the non-conductive lead body 216B and are electrically coupled to the proximal contacts 212B and 214B, respectively. However, in this example, a proximal end 223B of the second lead 107B is present within a second lead bore of the header 104B where the connectors 209B and 211B are present. The proximal end 223B includes proximal contacts 213B and 215B that electrically couple to the connectors 209B and 211B, respectively. Conductors 219B and 221B are shown in phantom for purposes of illustration as they are contained within the non-conductive lead body 217B and are electrically coupled to the proximal contacts 213B and 215B, respectively While the conductors 218B and 220B of lead 106B and the conductors 219B and 221B of lead 107B are shown as being linear, it will be appreciated that these conductors may instead be coiled in either or both leads. In either case, the conductors of each lead 106B and 107B are electrically isolated from one another such as via a non-conductive jacket and/or coating about each conductor.

As with the lead 106A of FIG. 2A, because the leads 106B and 107B include only two conductors each even though there are more than two distal electrodes, the amount of space required for the set of conductors is less than for a lead that utilizes a separate conductor for each distal electrode. Therefore, the lead body 216B and the lead body 117B may be made smaller than would be typical, or alternatively, the conductors of each lead may be made with a thicker filar than would be typical. Additionally, where the conductors of either or both of the leads 106B, 107B are coiled, the pitch of the conductors forming the coil may be tighter than would be typical for a lead with a separate conductor for each distal electrode.

As discussed in more detail below with reference to FIGS. 3A and 3B, the distal end of the leads 106B and 107B may include several electrodes even though there are only two conductors per lead carrying the stimulation signal to the distal end of the leads 106B, 107B. One or both conductors of each lead may be electrically coupled to multiple distal electrodes, where one conductor such as conductor 218B of lead 106B and 219B of lead 107B is a stimulation conductor providing the delivery path while the other conductor 220B of lead 106B and 221B of lead 107B is a stimulation conductor providing the return path.

The consequence of this configuration of multiple electrodes per conductor of each lead is again that stimulation is being provided across the entire region(s) 112 that the distal electrodes of the two leads span, as opposed to being provided only at a single target point within the region 112. The same paresthesia effect where the stimulation pulse frequency from each lead 106B, 107B is in the typical range of tens or hundreds of Hertz may occur. However, this paresthesia may be alleviated for either or both leads 106B, 107B by utilizing the alternative forms of stimulation therapy in either or both leads, like having the stimulation pulse frequency in the hundreds of kilohertz for example, where paresthesia is not felt with therapy.

Figure 2C:
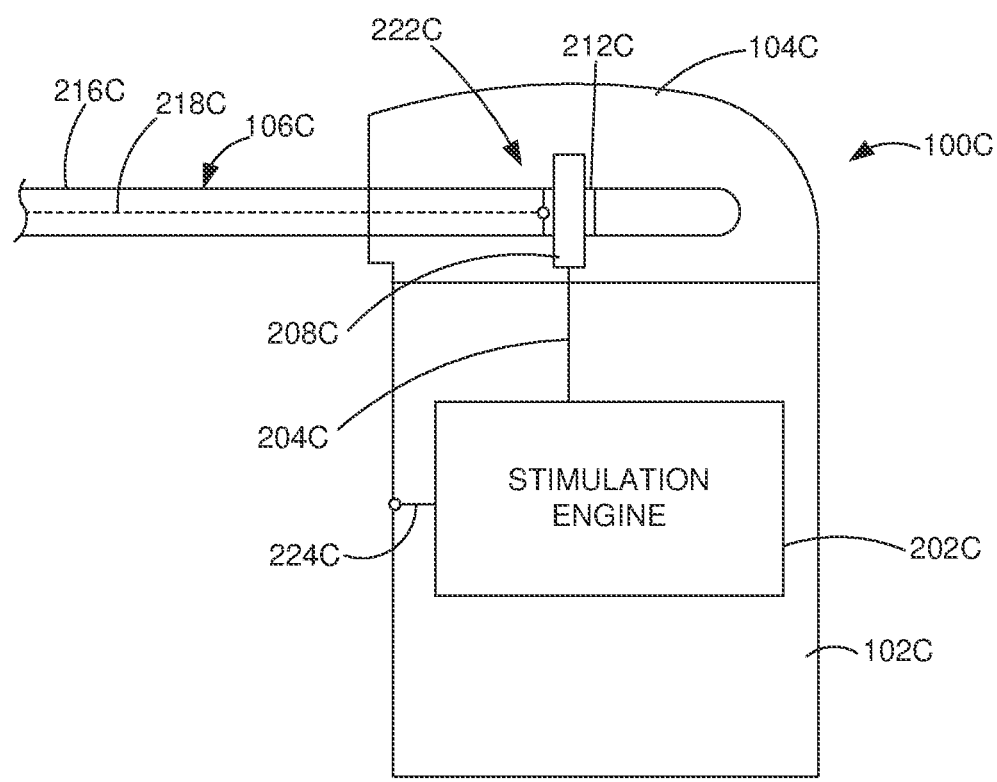
FIG. 2C shows a third example of an implantable medical system that includes a medical device coupled to an embodiment of an implantable percutaneous medical lead.

FIG. 2C shows a configuration of an implantable medical system 100C where medical device 102C includes a stimulation engine 202C that generates the stimulation pulses. In this example, the stimulation engine 202C is configured for unipolar stimulation of a single output by outputting stimulation pulses across header connector 208C and a chassis connection 224C, such as where connector 208C as a pulse delivery connector while the chassis connection 224C is a pulse return path, or vice versa. Device conductor 204C such as a lead frame conductor, feedthrough pin, and combinations thereof, carry the stimulation pulse signal between the stimulation engine 202C and the connector 208C by transitioning into the header 104C. While FIG. 2C shows a single output pair via the pairing of device conductor 204C and chassis connection 224C that are being used for the stimulation therapy, the stimulation engine 202C may have additional stimulation outputs although they may remain inactive.

A proximal end 222C of the lead 106C is configured to be mechanically coupled to the medical device 102C where it is present and affixed within a lead bore of the header 104C where the connector 208C is present. The proximal end 222C includes a proximal contact 212C that electrically couples to the connector 208C. Conductor 218C is shown in phantom for purposes of illustration as it is contained within the non-conductive lead body 216C and is electrically coupled to the proximal contact 212C. While the conductor 218C is shown as being linear, it will be appreciated that this conductor 218C may instead be coiled. In either case, the conductor 218C may include electrical isolation from any surrounding electrical paths via a non-conductive jacket and/or coating about the conductor.

Because the lead 106C includes only one conductor 218C even though there are multiple distal electrodes, the amount of space required for the conductor is less than for a lead that utilizes multiple conductors. Therefore, the lead body 216C may be made even smaller, or alternatively, the conductor 218C may be made with a thicker filar than would be typical. For example, the conductor 218C may have a thickness of more than 0.004 inch for a lead body diameter of 0.052 inch or less. Additionally, where the conductor 218C is coiled, the pitch may be tighter than would be typical for a lead with multiple conductors.

As discussed in more detail below with reference to FIG. 3C, the distal end of the lead 106C may include several electrodes even though there is only one conductors 218C carrying the stimulation signal to the distal end of the lead 106C. The conductor 218C may be electrically coupled to multiple distal electrodes, where the conductor 218C is a stimulation conductor providing the delivery path or the return path while the device 102 completes the path in conjunction with intervening body fluids and tissues.

The consequence of this configuration of multiple electrodes for the one conductor 218C is again that stimulation is being provided across the entire region 112 that the distal electrodes span, as opposed to being provided only at a single target point within the region 112. The same paresthesia effect where the stimulation pulse frequency from each lead 106B, 107B is in the typical range of tens or hundreds of Hertz may occur. However, as previously discussed, this paresthesia may be alleviated by utilizing alternative forms of stimulation therapy in the lead 106C such as by the stimulation pulse frequency being in the hundreds of kilohertz for example.

Figure 2D:
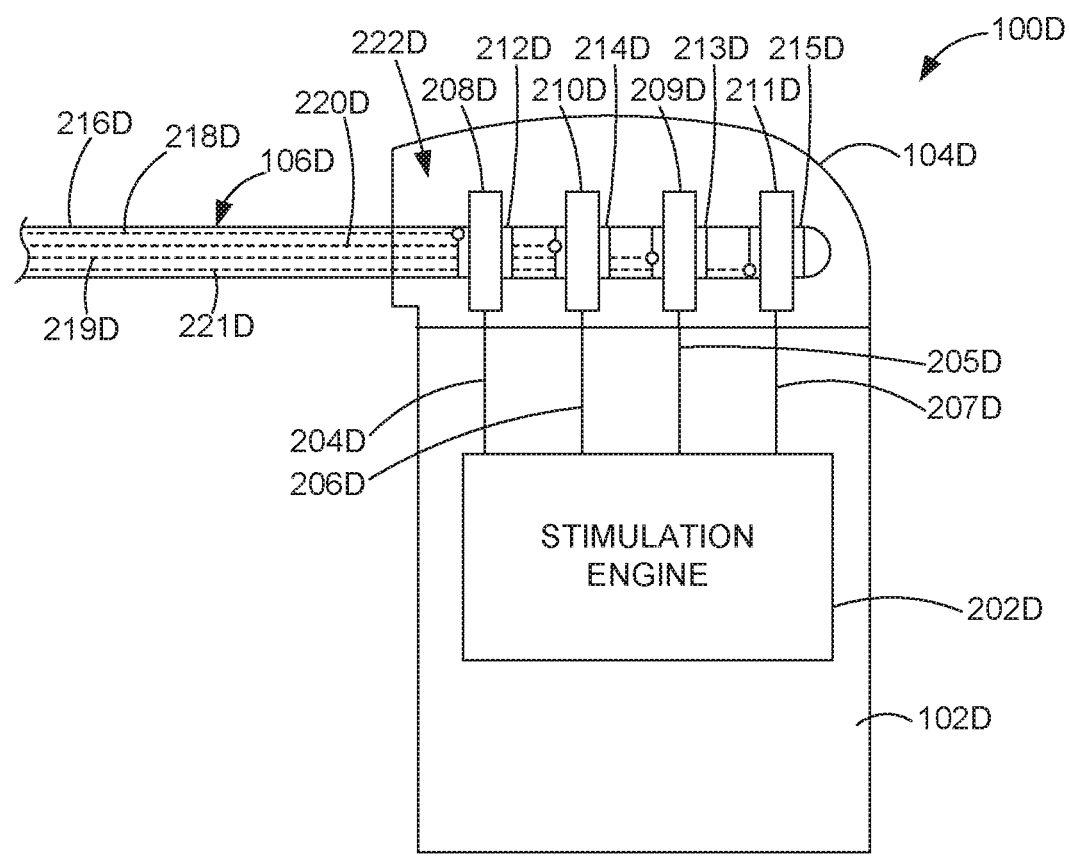
FIG. 2D shows a fourth example of an implantable medical system that includes a medical device coupled to an embodiment of an implantable percutaneous medical lead.

FIG. 2D shows a configuration of an implantable medical system 100D where medical device 102D includes a stimulation engine 202D that generates two different waveforms of stimulation pulses. In this example, the stimulation engine 202D is configured for bipolar stimulation of two output pairs by outputting stimulation pulses across header connectors 208D and 210D and also across header connectors 209D and 211D within the header 104D. In this example, the connectors 208D and 209D may act as pulse delivery connectors while connectors 210D and 211D are pulse return connectors. Device conductors 204D, 205D, 206D, and 207D such as lead frame conductors, feedthrough pins, and combinations thereof, carry the stimulation pulse signal between the stimulation engine 202D and the connectors 208D, 209D, 210D, and 211D by transitioning into the header 104D. While FIG. 2D shows two output pairs via the pairing of device conductors 204D, 205D, 206D, and 207D that are being used for the stimulation therapy, the stimulation engine 202D may have additional stimulation outputs although they may remain inactive.

When providing stimulation therapy via multiple waveforms on a single lead such as the two separate waveform outputs of lead 106D, the stimulation engine 202D may be configured in various ways. For instance, where the two lead outputs are stimulating different areas requiring therapy, it may be beneficial to have two different stimulation waveforms, one per lead, where the pulses of the waveforms may differ in amplitude, duration, or frequency. Thus, the stimulation engine 202D is configured to produce one waveform across one output pair 204D, 206D while being configured to produce a different waveform across another output pair 205D, 207D.

A proximal end 222D of the lead 106D is configured to be mechanically coupled to the medical device 102D where it is present and affixed within a lead bore of the header 104D where the connectors 208D, 209D, 210D, and 211D are present. The proximal end 222D includes proximal contacts 212D, 214D, 213D, and 215D that electrically coupled to the connectors 208D, 210D, 209D, and 211D, respectively. Conductors 218D, 219D, 220D, and 221D are shown in phantom for purposes of illustration as they are contained within the non-conductive lead body 216D and are electrically coupled to the proximal contacts 212D, 213D, 214D, and 215D, respectively. While the conductors are shown as being linear, it will be appreciated that these conductors may instead be coiled. In either case, the conductors are electrically isolated from one another such as via a non-conductive jacket and/or coating about each conductor.

Because the lead 106D includes four conductors even though there are more than four distal electrodes, the amount of space required for the set of conductors is less than for a lead that utilizes a separate conductor for each distal electrode. Therefore, the lead body 216D may be made smaller than would be typical, or alternatively, the conductors may be made with a thicker filar than would be typical as discussed above for the prior embodiments. Additionally, where the conductors are coiled, the pitch may be tighter than would be typical for a lead with a separate conductor for each distal electrode.

As discussed in more detail below with reference to FIG. 3D, the distal end of the lead 106D may include several electrodes even though there are only four conductors carrying the stimulation signal to the distal end of the lead 106D. One or more of the four conductors may be electrically coupled to multiple distal electrodes, where two conductors such as conductors 218D and 219D are stimulation conductors providing the delivery paths for the two stimulation waveforms while the other conductors 220D and 221D are stimulation conductors providing the return path.

The consequence of this configuration of multiple electrodes for one or more conductors is again that stimulation is being provided across the entire region 112 that the distal electrodes span, as opposed to being provided only at a single target point within the region 112. Indeed, the presence of two stimulation waveforms may be used to treat multiple target sites within the region 112 that call for distinctions in the stimulation waveforms. However, the same paresthesia effect where the stimulation pulse frequency of each waveform from the lead 106D is in the typical range of tens or hundreds of Hertz may occur for both stimulation waveforms. However, as previously discussed, this paresthesia may be alleviated by utilizing alternative forms of stimulation therapy in the lead 106D such as by the stimulation pulse frequency of one or both stimulation waveforms being in the hundreds of kilohertz for example.

Figure 2E:
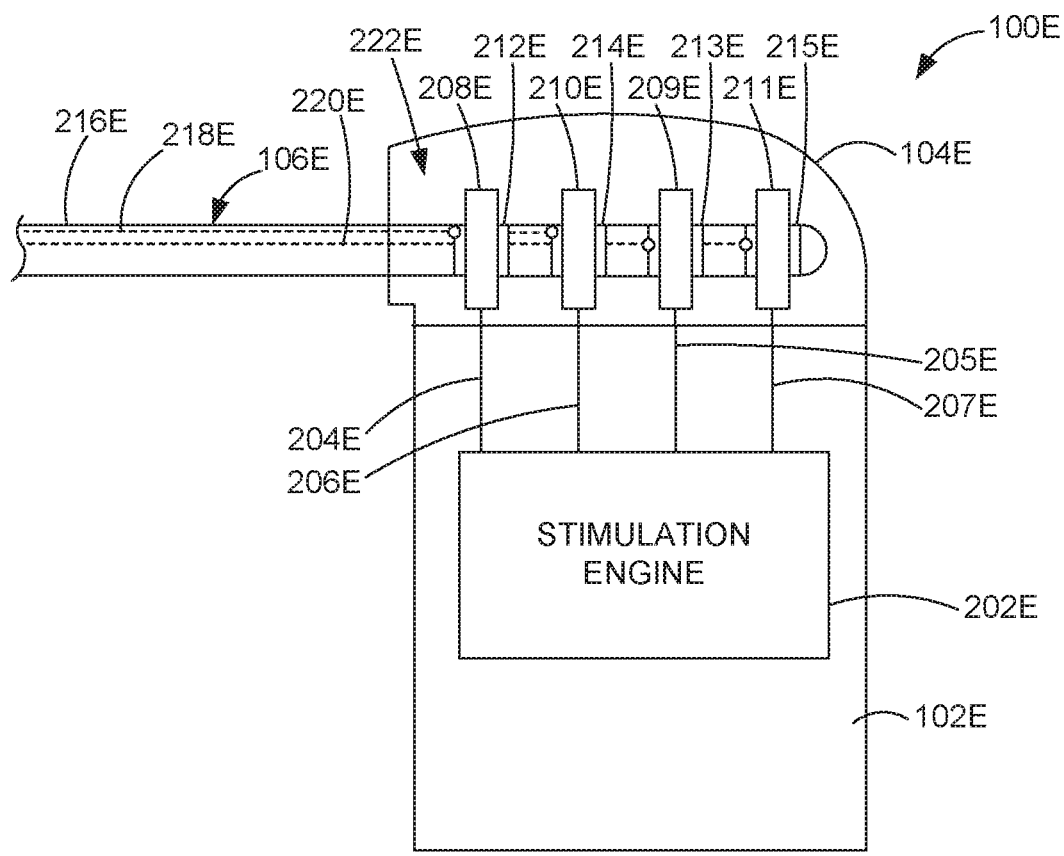
FIG. 2E shows a fifth example of an implantable medical system that includes a medical device coupled to an embodiment of an implantable percutaneous medical lead.

FIG. 2E shows a configuration of an implantable medical system 100E where medical device 102E includes a stimulation engine 202E that generates a waveform of stimulation pulses. In this example, the stimulation engine 202E is configured for bipolar stimulation of two identical output pairs by outputting identical stimulation pulses across header connectors 208E and 209E and across header connectors 210E and 211E within the header 104E. In this example, the connectors 208E and 210E may act as pulse delivery connectors while connectors 209E and 211E are pulse return connectors. Device conductors 204E, 205E, 206E, and 207E such as lead frame conductors, feedthrough pins, and combinations thereof, carry the stimulation pulse signal between the stimulation engine 202E and the connectors 208E, 209E, 210E, and 211E by transitioning into the header 104E. While FIG. 2E shows two output pairs via the pairing of device conductors 204E, 205E, 206E, and 207E that are being used for the stimulation therapy, the stimulation engine 202E may have additional stimulation outputs that may remain inactive or may also electrically couple to the conductors of the lead 106E in a similar manner.

A proximal end 222E of the lead 106E is configured to be mechanically coupled to the medical device 102E where it is present and affixed within a lead bore of the header 104E where the connectors 208E, 209E, 210E, and 211E are present. The proximal end 222E includes proximal contacts 212E, 214E, 213E, and 215E that electrically coupled to the connectors 208E, 210E, 209E, and 211E, respectively. Conductors 218E and 220E are shown in phantom for purposes of illustration as they are contained within the non-conductive lead body 216E. Conductor 218E is electrically coupled to both the proximal contact 212E and the proximal contact 214E, while conductor 220E is electrically coupled to both the proximal contact 213E and the proximal contact 215E. Because the conductors 218E and 220E are coupled across two output pairs of the stimulation engine 202E, the conductors 218E and 220E thereby carry double the electrical current from the stimulation engine 202E than if coupled to only a single output pair. While the conductors are shown as being linear, it will be appreciated that these conductors may instead be coiled. In either case, the conductors are electrically isolated from one another such as via a non-conductive jacket and/or coating about each conductor.

Because the lead 106E includes four conductors even though there are more than four distal electrodes, the amount of space required for the set of conductors is less than for a lead that utilizes a separate conductor for each distal electrode. Therefore, the lead body 216E may be made smaller than would be typical, or alternatively, the conductors may be made with a thicker filar than would be typical as discussed above for the prior embodiments. Additionally, where the conductors are coiled, the pitch may be tighter than would be typical for a lead with a separate conductor for each distal electrode.

As discussed in more detail below with reference to FIGS. 3A and 3B, the distal end of the lead 106E may include several electrodes even though there are only two conductors carrying the stimulation signal to the distal end of the lead 106E. One or more of the two conductors may be electrically coupled to multiple distal electrodes, where one conductor such as conductor 218E is a stimulation conductor providing the delivery path for the stimulation waveform while the other conductor 220E is a stimulation conductor providing the return path.

The consequence of this configuration of multiple electrodes for one or more conductors is again that stimulation is being provided across the entire region 112 that the distal electrodes span, as opposed to being provided only at a single target point within the region 112. However, as previously discussed, paresthesia may be alleviated by utilizing alternative forms of stimulation therapy in the lead 106D such as by the stimulation pulse frequency of one or both stimulation waveforms being in the hundreds of kilohertz for example.

Figure 3A:
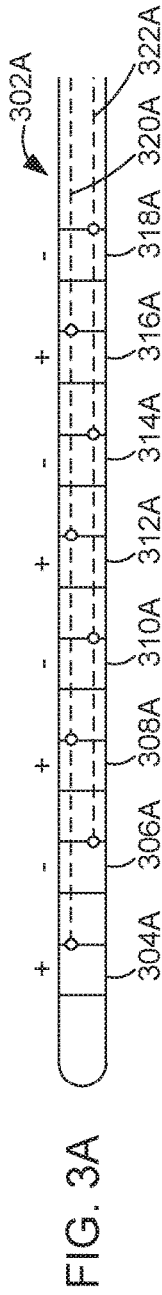
FIG. 3A shows a first example of a distal end of an embodiment of an implantable percutaneous medical lead.

FIG. 3A shows a distal end 302A of a lead where there are more distal electrodes than conductors. As can be seen, in this example there are two conductors 320A and 322A while there are eight distal electrodes 304A, 306A, 308A, 310A, 312A, 314A, 316A, and 318A. It will be appreciated that while eight distal electrodes are shown for this specific example, any number of distal electrodes are applicable. These distal electrodes are ring-shaped in this example and are known as ring electrodes, where the ring may fully or partially encircle the lead body. The lead 106 that includes this distal end 302A is referred to as a percutaneous lead because it may be implanted using percutaneous methods by virtue of using ring electrodes that encircle the lead body.

Each conductor of this example of FIG. 3A creates a path to multiple distal electrodes. For instance, conductor 320A creates a path to a set of distal ring electrodes 304A, 308A, 312A, and 316A. Conductor 322A creates a path to a set of distal ring electrodes 306A, 310A, 314A, and 318A. This configuration results in the interleaving of the two sets of distal electrodes which provides interleaved electrical nodes as illustrated by the +−+− labels. The electrodes are separated by sections of lead body so that the stimulation pulses must travel into the surrounding body tissue to traverse from one node to an adjacent node.

This distal end 302A of FIG. 3A may be the distal end of the lead 106A of FIG. 2A as well as the distal end of the leads 106B and 107B from FIG. 2B, and 106E from FIG. 2E. In the case of lead 106A, conductors 320A and 322A correspond to conductors 218A and 220A. In the case of lead 106B, conductors 320A and 322A correspond to conductors 218B and 220B. In the case of lead 107B, conductors 320A and 322A correspond to conductors 219B and 221B.

The distal electrodes on the distal end 302A may have typical ring electrode dimensions in order to span multiple vertebral segments. For instance, as a first specific example that is not intended to be limiting, the distal electrode rings may have an axial length in the range of 0.100 to 0.15 inch while the axial spacing between nearest edge to nearest edge of adjacent distal electrode rings may be in the range of 0.050 to 0.075 inch. In this non-limiting specific example, the number of distal electrodes may be eight and the total electrode distance, as measured from the distal end of the most distal electrode to the proximal end of the most proximal electrode is in the range of 1.250 to 1.500 inch, and thereby span in excess of a thoracic segment. In a second non-limiting specific example, with the same sized eight distal ring electrodes but with an electrode spacing in the range of 0.150 to 0.175 inch, the total electrode distance in the range of 2 to 2.25 inch spans two thoracic segments. In a third non-limiting specific example, with the same sized distal ring electrodes and with the same 0.150 to 0.175 inch spacing but with a total of 16 distal electrodes, the total electrode distance in the range of 4 to 4.500 inch spans four thoracic segments. Examples that span in excess of four thoracic or other vertebral segments are also applicable.

Figure 3B:
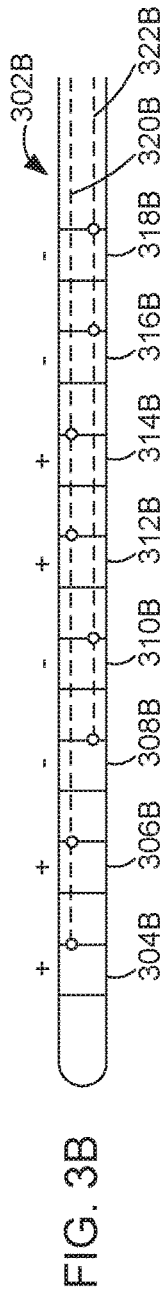
FIG. 3B shows a second example of a distal end of an embodiment of an implantable percutaneous medical lead.

FIG. 3B shows a distal end 302B of a lead where there are more distal electrodes than conductors. As can be seen, in this example there are two conductors 320B and 322B while there are eight distal electrodes 304B, 306B, 308B, 310B, 312B, 314B, 316B, and 318B. It will be appreciated that while eight distal electrodes are shown for this specific example, any number of distal electrodes are applicable. These distal electrodes are also ring-shaped in this example where the ring may fully or partially encircle the lead body. The lead 106 that includes this distal end 302B is referred to as a percutaneous lead as stated above.

Each conductor of this example of FIG. 3B also creates a path to multiple distal electrodes. For instance, conductor 320A creates a path to a set of distal ring electrodes 304B, 306B, 312B, and 314B. Conductor 322A creates a path to a set of distal ring electrodes 308B, 310B, 316B, and 318B. This configuration results in a modified interleaving of the two sets of distal electrodes where pairs of electrodes are formed based on node type and then pairs are interleaved. This interleaving of pairs based on node type create interleaving of paired electrical nodes as illustrated by the ++--++-- labels. The electrodes here are separated by sections of lead body so that the stimulation pulses must travel into the surrounding body tissue to traverse from one node to an adjacent node of differing node type.

This distal end 302B of FIG. 3B may be the distal end of the lead 106B of FIG. 2A as well as the distal end of the leads 106B and 107B from FIG. 2B and lead 106E from FIG. 2E. In the case of lead 106A, conductors 320B and 322B correspond to conductors 218A and 220A. In the case of lead 106B, conductors 320B and 322B correspond to conductors 218B and 220B. In the case of lead 107B, conductors 320B and 322B correspond to conductors 219B and 221B.

The non-limiting specific examples of distal electrode ring size and spacing discussed above in relation to distal end 302A of FIG. 3A also apply to the distal end 302B. As stated above, those specific examples produce an electrode distance that spans in excess of a thoracic segment up to four thoracic segments. Examples that span in excess of four thoracic or other vertebral segments are also applicable.

Figure 3C:
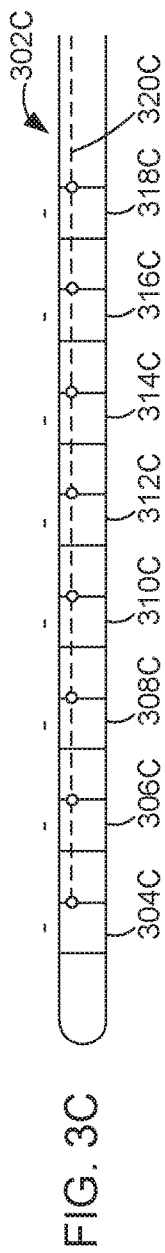
FIG. 3C shows a third example of a distal end of an embodiment of an implantable percutaneous medical lead.

FIG. 3C shows a distal end 302C of a lead where there are more distal electrodes than conductors. As can be seen, in this example there is one conductor 320C while there are eight distal electrodes 304C, 306C, 308C, 310C, 312C, 314C, 316C, and 318C. It will be appreciated that while eight distal electrodes are shown for this specific example, any number of distal electrodes are applicable. These distal electrodes are also ring-shaped in this example where the ring may fully or partially encircle the lead body. The lead 106 that includes this distal end 302C is referred to as a percutaneous lead as stated above.

The conductor 320C of this example of FIG. 3C also creates a path to all the distal electrodes shown. This proximal end 302C is therefore directed to unipolar stimulation where all the distal electrodes have the same node type, in this case cathodes as illustrated by the ---- labels. The opposite node type from the node type of the distal electrodes shown is provided by the housing of the medical device 102. The electrodes here may be separated by sections of lead body as well.

This distal end 302C of FIG. 3C may be the distal end of the lead 106C of FIG. 2C. In that configuration, conductor 320C correspond to conductors 218C.

The non-limiting specific examples of distal electrode ring size and spacing discussed above in relation to distal end 302A of FIG. 3A also apply to the distal end 302C. As stated above, those specific examples produce an electrode distance that spans in excess of a thoracic segment up to four thoracic segments. Examples that span in excess of four thoracic or other vertebral segments are also applicable.

It will be appreciated that unipolar stimulation discussed above for FIG. 3C can also be achieved in leads that are capable of bipolar stimulation by having only a subset of the electrodes by electrically coupled to an active stimulation output of the stimulation engine of the medical device 102. For instance, the leads shown in FIGS. 3A and 3B could provide unipolar stimulation by having only one of the conductors 320A or 322B of FIG. 3A or only one of the conductors 320B or 322B of FIG. 3B be active.

Figure 3D:
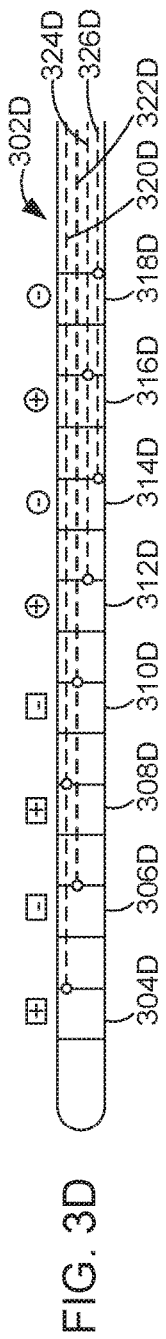
FIG. 3D shows a fourth example of a distal end of an embodiment of an implantable percutaneous medical lead.

FIG. 3D shows a distal end 302D of a lead where there are more distal electrodes than conductors. As can be seen, in this example there are four conductors 320D, 322D, 324D, and 326D while there are eight distal electrodes 304D, 306D, 308D, 310D, 312D, 314D, 316D, and 318D. It will be appreciated that while eight distal electrodes are shown for this specific example, any number of distal electrodes are applicable. These distal electrodes are also ring-shaped in this example where the ring may fully or partially encircle the lead body. The lead 106 that includes this distal end 302D is also a percutaneous lead.

Each conductor of this example of FIG. 3D creates a path to multiple distal electrodes. There are four conductors to achieve to separate stimulation waveforms. Thus, one set of the distal electrodes provides one of the stimulation waveforms while another set of the distal electrodes provides the other. For instance, conductors 320D and 322D may provide a first stimulation waveform. Conductor 320D creates a path to a subset of distal ring electrodes 304D and 308D while conductor 322D creates a path to a subset of distal ring electrodes 306D and 310D. This configuration results in the interleaving of these two subsets of distal electrodes which provides interleaved electrical nodes as illustrated by the +-+- labels within squares for the first stimulation waveform. These electrodes are separated by sections of lead body so that the stimulation pulses must travel into the surrounding body tissue to traverse from one node to an adjacent node.

Conductors 324D and 326D may provide a second stimulation waveform. Conductor 324D creates a path to a subset of distal ring electrodes 312D and 316D while conductor 326D creates a path to a subset of distal ring electrodes 314D and 318D. This configuration results in the interleaving of these two subsets of distal electrodes which provides interleaved electrical nodes as illustrated by the +−+− labels within circles for the second stimulation waveform. These electrodes are also separated by sections of lead body so that the stimulation pulses must travel into the surrounding body tissue to traverse from one node to an adjacent node.

This distal end 302D of FIG. 3D may be the distal end of the lead 106D of FIG. 2D. In the case of lead 106D, conductors 320D and 322D correspond to conductors 218D and 220D for the first stimulation waveform output while conductors 324D and 326D correspond to conductors 219D and 221D for the second stimulation waveform output.

The non-limiting specific examples of distal electrode ring size and spacing discussed above in relation to distal end 302A of FIG. 3A also apply to the distal end 302D. As stated above, those specific examples produce an electrode distance that spans in excess of a thoracic segment up to four thoracic segments. Examples that span in excess of four thoracic or other vertebral segments are also applicable.

Figure 3E:
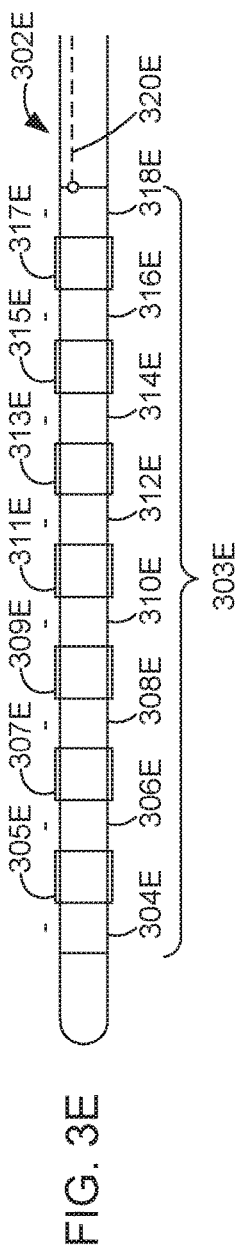
FIG. 3E shows a fifth example of a distal end of an embodiment of an implantable percutaneous medical lead.

FIG. 3E shows a distal end 302E of a percutaneous lead where there are more distal electrodes than conductors. As can be seen, in this example there is one conductor 320E while there are eight distal electrodes 304E, 306E, 308E, 310E, 312E, 314E, 316E, and 318E. It will be appreciated that while eight distal electrodes are shown for this specific example, any number of distal electrodes are applicable. However, rather than being individual rings, the distal electrodes are one relatively long distal ring 303E that is electrically coupled to the conductor 320E. To create the individual distal electrodes 304E, 306E, 308E, 310E, 312E, 314E, 316E, and 318E, there are a plurality of insulator bands 305E, 307E, 309E, 311E, 313E, 315E, and 317E attached onto the distal ring 303E. To provide better flexibility in certain implantations, such as for spinal cord stimulation, it may be desirable to have fewer electrodes per distal ring 303E, such as two electrodes per distal ring 303E, and then include multiple distal rings like distal ring 303E where one or more distal rings have at least one insulator band to provide multiple distal electrodes per distal ring.

The conductor 320E of this example of FIG. 3E creates a path to all the individual distal electrodes formed from the single distal ring 303E as shown. This proximal end 302E is therefore directed to unipolar stimulation where all the distal electrodes have the same node type, in this case cathodes as illustrated by the −−−− labels. The opposite node type from the node type of the distal electrodes shown is provided by the housing of the medical device 102.

This distal end 302E of FIG. 3E may be the distal end of the lead 106C of FIG. 2C. In that configuration, conductor 320E correspond to conductors 218C.

The non-limiting specific examples of distal electrode ring size and spacing discussed above in relation to distal end 302A of FIG. 3A also apply to the distal end 302E. As stated above, those specific examples produce an electrode distance that spans in excess of a thoracic segment up to four thoracic segments. Examples that span in excess of four thoracic or other vertebral segments are also applicable.

While the example of FIG. 3E is a unipolar configuration with a single ring 303E, it will be appreciated that multiple rings that have insulative bands forming multiple electrodes per ring may be utilized. For instance, in the example of FIG. 3B, electrodes 304B and 306B may provided via a single ring with an insulative band between in the middle to expose the portions of the single ring that provide the electrodes 304B and 306B. Furthermore, a second single ring may provide the electrodes 308B, 310B, a third single ring may provide the electrodes 312B, 314B, and a fourth single ring may provide the electrodes 316B, 318B.

In some cases, it may be beneficial to utilize a lead extension between the medical device 102 and the lead 106, particularly where the distance from the medical device 102 to the region 112 is relatively large and the lead 106 cannot cover the entire distance. In such a case, leads having fewer conductors than distal electrodes may make use of conventional lead extensions. However, lead extensions having fewer conductors than the number of distal connectors on the lead may also be used. Where embodiments of the lead extension are provided with fewer conductors than distal connectors and/or proximal contacts and those conductors are cables rather than coils, the diameter of the body of the embodiments of the lead extension may be significantly smaller than conventional lead extensions considering the embodiments of the lead extension need not include a stylet lumen.

Figure 4A:
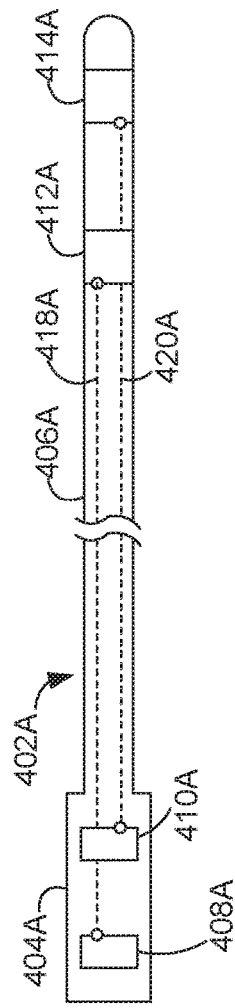
FIG. 4A shows an example of an embodiment of an implantable medical lead extension that may be used with an embodiment of the implantable medical lead that has fewer conductors than distal electrodes.

As shown in the example of FIG. 4A, a lead extension 402A may include two proximal contacts 412A, 414A that connect to the stimulation engine output of the medical device 102, such as medical device 102A of FIG. 2A or medical device 102B of FIG. 2B. The lead extension 402A may include a distal connector portion 404A that includes two distal connectors 408A, 410A. Thus, a lead utilizing only two conductors such as lead 106A, lead 106B, and/or lead 107B may utilize this lead extension 402A together with medical device 102A or 102B. For instance, the lead 106A of FIG. 2A having distal end 302A of FIG. 3A or distal end 302B of FIG. 3B may connect to the distal end 404A.

The stimulation signal is carried between the connector 208A and the conductor 320A or 320B via proximal contact 412A, conductor 418A, and distal connector 408A coupled to the proximal contact 212A. The stimulation signal is further carried between the connector 210A and the conductor 322A or 322V via proximal contact 414A, conductor 420A, and distal connector 410A coupled to the proximal contact 214A. Conductors 418A and 420A are shown in phantom for purposes of illustration as they are contained within the non-conductive lead extension body 406A and are electrically coupled to the proximal contacts 412A and 414A, respectively. While the conductors 418A and 420A are shown as being linear, it will be appreciated that these conductors 418A and 420A may instead be coiled. In either case, the conductors 418A and 420A are electrically isolated from one another such as via a non-conductive jacket and/or coating about each conductor.

Additionally, even where the lead 106 is a conventional lead with a same number of conductors as distal electrodes, a lead extension coupled to the lead 106 may utilize fewer conductors than distal connectors. For instance, an example of a lead extension 402B shown in FIG. 4B includes two conductors 418B and 420B that are coupled to two proximal contacts 412B and 414B, respectively. However, within a distal portion 404B, there are four distal connectors 408B, 410B, 409B, and 411B.

Thus, a lead having four proximal contacts, four conductors, and four distal electrodes may connect to the lead extension 402B. The four proximal contacts of the lead connect to the four distal connectors. Each conductor of this example of FIG. 4B creates a path to multiple distal connectors. For instance, conductor 418B creates a single path for a set of distal connectors 408B and 409B. Conductor 420B creates a path to a set of distal connectors 410B and 411B. Thus, the stimulation signal carried by the conductor 420B is applied to multiple distal connectors of the lead extension 402B which then also applies the stimulation signal to multiple distal electrodes of the lead. This configuration results in the distal electrodes of the lead being activated as if the lead itself had multiple distal electrodes grouped to a single conductor like the leads of FIGS. 3A-3D.

Conductors 418B and 420B are shown in phantom for purposes of illustration as they are contained within the non-conductive lead extension body 406B and are electrically coupled to the proximal contacts 412B and 414B, respectively. While the conductors 418B and 420B are shown as being linear, it will be appreciated that these conductors 418B and 420B may instead be coiled. In either case, the conductors 418B and 420B are electrically isolated from one another such as via a non-conductive jacket and/or coating about each conductor.

Because the lead extensions 402A and 402B include two conductors even though there are more than two distal electrodes on the lead that can be coupled to the lead extensions 402A and 402B, the amount of space within the lead extension required for the set of conductors is less than for a lead extension that utilizes a separate conductor for each distal electrode. Therefore, the lead extension body 406A, 406B that contains the conductors may be made smaller than would be typical, or alternatively, the conductors may be made with a thicker filar than would be typical. Additionally, where the conductors are coiled, the pitch may be tighter than would be typical for a lead extension with a separate conductor for each distal electrode of the lead coupled to the lead extension.

Figure 4B:
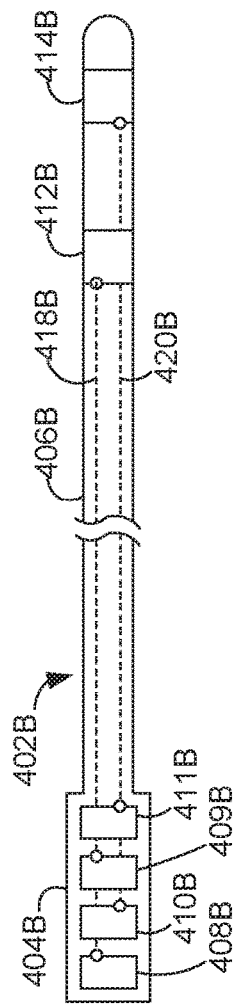
FIG. 4B shows an example of an embodiment of an implantable medical lead extension that includes fewer conductors than distal connectors.
Figure 4C:
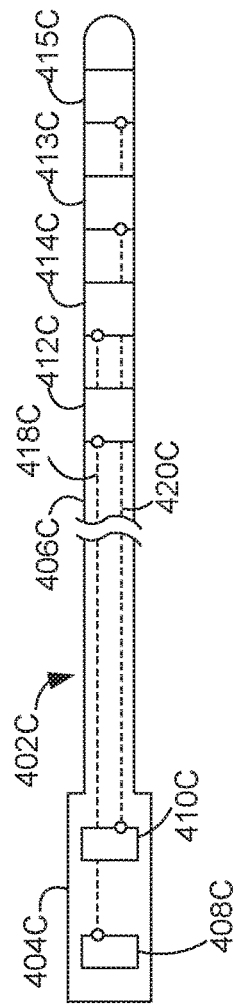
FIG. 4C shows another example of an embodiment of an implantable medical lead extension that may be used with an embodiment of the implantable medical lead that has fewer conductors than distal electrodes.

Another set of examples of lead extensions that use reduced numbers of conductors are shown in FIGS. 4A and 4B, where multiple output pairs of a stimulation engine, like that shown in FIG. 2E, are used to produce identical waveforms and thereby increase the current per lead conductor. As shown in the example of FIG. 4C, a lead extension 402C may include four proximal contacts 412C, 414C, 413D, and 415D that connect to four corresponding stimulation engine outputs of the medical device 102, such as the medical device 102E of FIG. 2E. The lead extension 402C may include a distal connector portion 404E that includes two distal connectors 408C, 410C. Thus, a lead utilizing only two conductors such as lead 106A, lead 106B, and/or lead 107B may utilize this lead extension 402C together with medical device 102E. For instance, the lead 106A of FIG. 2A having distal end 302A of FIG. 3A or distal end 302B of FIG. 3B may connect to the distal end 404C.

The stimulation signal is carried between the connectors 208E and 210E and the conductor 320A or 320B via proximal contacts 412C, 414C, conductor 418C, and distal connector 408C coupled to the proximal contact 212A. The stimulation signal is further carried between the connectors 209E and 211E and the conductor 322A or 322B via proximal contacts 413C and 415C, conductor 420C, and distal connector 410C coupled to the proximal contact 214A. Conductors 418C and 420C are shown in phantom for purposes of illustration as they are contained within the non-conductive lead extension body 406C and are electrically coupled to the proximal contacts 412C/414C and 413C/415C, respectively. While the conductors 418C and 420C are shown as being linear, it will be appreciated that these conductors 418C and 420C may instead be coiled. In either case, the conductors 418C and 420C are electrically isolated from one another such as via a non-conductive jacket and/or coating about each conductor.

Figure 4D:
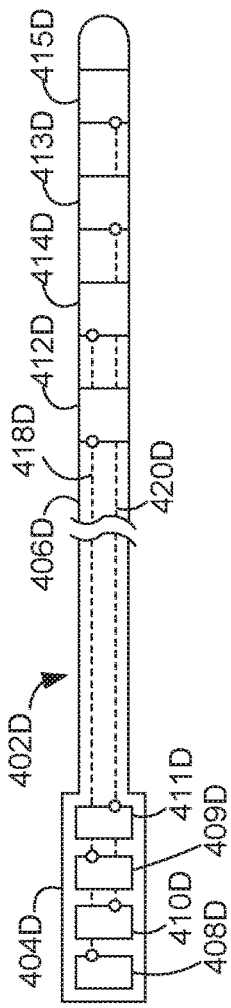
FIG. 4D shows another example of an embodiment of an implantable medical lead extension that includes fewer conductors than distal connectors.

Additionally, even where the lead 106 is a conventional lead with a same number of conductors as distal electrodes, a lead extension coupled to the lead 106 may utilize fewer conductors than distal connectors while utilizing multiple stimulation output pairs of the stimulation engine. For instance, lead extension 402D shown in FIG. 4D includes two conductors 418D and 420D that are coupled to four proximal contacts 412D, 414D, 413D, and 415D. However, within a distal portion 404D, there are four distal connectors 408D, 410D, 409D, and 411D.

Thus, a lead having four proximal contacts, four conductors, and four distal electrodes may connect to the lead extension 402D. The four proximal contacts of the lead connect to the four distal connectors. Each conductor of this example of FIG. 4D creates a path to multiple distal connectors. For instance, conductor 418D creates a single path for a set of distal connectors 408D and 409D. Conductor 420D creates a path to a set of distal connectors 410D and 411D. Thus, the stimulation signal carried by the conductor 420D is applied to multiple distal connectors of the lead extension 402D which then also applies the stimulation signal to multiple distal electrodes of the lead. This configuration results in the distal electrodes of the lead being activated as if the lead itself had multiple distal electrodes grouped to a single conductor like the leads of FIGS. 3A-3D.

Conductors 418D and 420D are shown in phantom for purposes of illustration as they are contained within the non-conductive lead extension body 406D and are electrically coupled to the proximal contacts 412D/414D and 413D/415D, respectively. While the conductors 418D and 420D are shown as being linear, it will be appreciated that these conductors 418D and 420D may instead be coiled. In either case, the conductors 418D and 420D are electrically isolated from one another such as via a non-conductive jacket and/or coating about each conductor.

Figure 5:
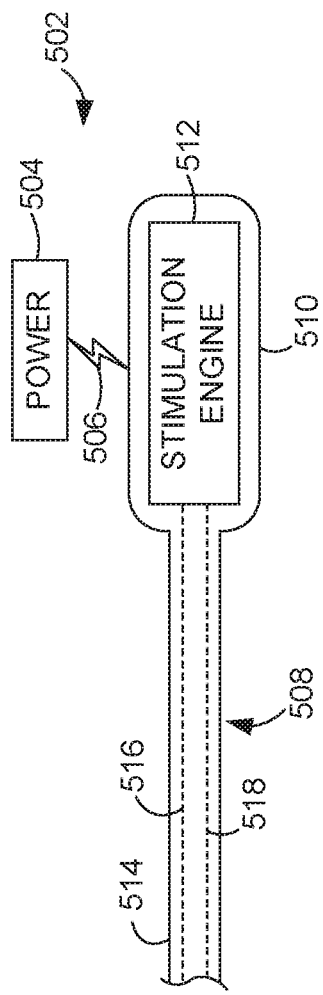
FIG. 5 shows an example of an embodiment of an implantable medical lead or extension that utilizes a self-contained stimulation engine and an external power source.

FIG. 5 shows an example of an alternate medical system 502 that may utilize a lead having fewer conductors than distal electrodes. In this example, the lead 508 includes a proximal end 520 that provides the mechanically coupled medical device that houses the stimulation engine 512 rather than the lead being connected to separate medical device 102. This proximal end 520 may remain small enough to be percutaneously implanted by lacking a battery. In order to power the stimulation engine 512, the stimulation engine electronics include a wireless power receiving circuit. An external power source 504 that outputs wireless power 506 is placed in proximity to the proximal end 510. The wireless power 506 is conveyed through any intervening skin and other tissues of the patient 110 to reach the stimulation engine 512.

Maintaining the power source 504 in proximity to the implanted stimulation engine 512 for long periods of time may be impractical. However, alternate forms of stimulation like those discussed above that utilize a pulse frequency of hundreds of kilohertz has been found to have a lasting effect after a short period of stimulation, where relatively long periods of time may occur before stimulation is needed again. Thus, by utilizing such stimulation therapy, the power source 504 is only needed periodically. Furthermore, as discussed above in relation to the various other embodiments of a medical system, by utilizing this alternate form of stimulation therapy, the paresthesia effects that would span the entire region 112 due to all distal electrodes of the lead 508 being actively used are alleviated.

In this example of FIG. 5, a lead body 514 that extends from the proximal end 510 contains conductors 516 and 518. These conductors are electrically coupled to the stimulation engine 512 to carry the stimulation pulses of the bipolar stimulation waveform. While the lead body 514 contains only the two conductors 516 and 518, the distal end of the lead body 514 includes more than two distal electrodes. For example, either the distal end 302A of FIG. 3A or the distal end 302B of FIG. 3B may be used as the distal end of the lead body 514. In the case of distal end 302A, conductor 320A corresponds to conductor 516 while conductor 322A corresponds to conductor 518. In the case of distal end 302B, conductor 320B corresponds to conductor 516 while conductor 322B corresponds to conductor 518.

While embodiments have been particularly shown and described, it will be understood by those skilled in the art that various other changes in the form and details may be made therein without departing from the spirit and scope of the invention.

What is claimed is:

1. An implantable percutaneous medical lead, comprising:
    a percutaneous lead body having a proximal area configured to physically couple to a medical device;
    a first proximal contact coupled to the proximal area of the lead body;
    a first plurality of distal ring electrodes being spaced apart along an axial dimension of the lead and coupled to a distal area of the lead body to configure the implantable percutaneous medical lead for spinal cord stimulation across multiple vertebral segments;
    a first conductor electrically coupled to the first proximal contact, extending through the lead body, and electrically coupled to the plurality of distal ring electrodes;
    a second proximal contact coupled to the proximal area of the percutaneous lead body;
    a second plurality of distal ring electrodes; and
    a second conductor electrically coupled to the second proximal contact, extending through the lead body, and electrically coupled to the second plurality of distal ring electrodes,
    wherein the first plurality of distal ring electrodes and the second plurality of distal ring electrodes are interleaved so that at least one distal ring electrode of the second plurality is located between two distal ring electrodes of the first plurality.

2. The implantable percutaneous medical lead of claim 1, wherein the first conductor and the first plurality of distal ring electrodes provide a delivery path for the stimulation pulse while the second conductor and the second plurality of distal ring electrodes provide a return path for the stimulation pulse.

3. The implantable percutaneous medical lead of claim 1, wherein the first conductor provides a delivery path and the second conductor provides a return path for a first stimulation pulse, the implantable medical lead further comprising:
    a third proximal contact coupled to the proximal area of the percutaneous lead body;
    a third plurality of distal ring electrodes being spaced apart along an axial dimension of the percutaneous lead body and coupled to a distal area of the percutaneous lead body; and
    a third conductor electrically coupled to the third proximal contact, extending through the percutaneous lead body, and electrically coupled to the third plurality of distal ring electrodes, the third conductor providing a delivery path for a second stimulation pulse.

4. The implantable percutaneous medical lead of claim 1, wherein the plurality of distal electrodes are provided by a single ring and at least one insulator band located on the single ring, and wherein the first conductor is electrically coupled to the plurality of distal ring electrodes by a single physical connection to the single ring.

5. An implantable medical system, comprising:
    a medical device having a stimulation engine; and
    a first implantable percutaneous medical lead, comprising:
        a percutaneous lead body mechanically coupled to the medical device;
        a plurality of distal ring electrodes being spaced apart along an axial dimension of the percutaneous lead body and coupled to a distal area of the percutaneous lead body to configure the implantable percutaneous medical lead for spinal cord stimulation across multiple vertebral segments;
        a first conductor electrically coupled to the stimulation engine, extending through the percutaneous lead body, and electrically coupled to the plurality of distal ring electrodes;
        a second plurality of distal ring electrodes coupled to the distal area of the percutaneous lead body; and
        a second conductor electrically coupled to the stimulation engine, extending through the percutaneous lead body, and electrically coupled to the second plurality of distal ring electrodes,
        wherein the first plurality of distal ring electrodes and the second plurality of distal ring electrodes are interleaved so that at least one distal ring electrode of the second plurality is located between two distal ring electrodes of the first plurality.

6. The implantable medical system of claim 5, wherein the first conductor and the first plurality of distal ring electrodes provide a delivery path for the stimulation pulse while the second conductor and the second plurality of distal ring electrodes provide a return path for the stimulation pulse.

7. The implantable medical system of claim 5, wherein the first implantable medical lead further comprises:
    a third plurality of distal ring electrodes being spaced apart along an axial dimension of the percutaneous lead body and coupled to the distal area of the percutaneous lead body; and
    a third conductor electrically coupled to the stimulation engine, extending through the percutaneous lead body, and electrically coupled to the third plurality of distal ring electrodes, the third conductor providing a delivery path for a second stimulation pulse.

8. The implantable medical system of claim 5, further comprising a second implantable percutaneous medical lead, comprising:
    a percutaneous lead body of the second implantable percutaneous medical lead;
    a plurality of distal ring electrodes of the second implantable percutaneous medical lead being spaced apart along an axial dimension of the percutaneous lead body of the second implantable percutaneous medical lead and coupled to a distal area of the percutaneous lead body of the second implantable percutaneous medical lead; and
    a first conductor of the second implantable percutaneous medical lead electrically coupled to the stimulation engine, extending through the percutaneous lead body of the second implantable percutaneous medical lead, and electrically coupled to the plurality of distal ring electrodes of the second implantable percutaneous medical lead.

9. The implantable medical system of claim 8, wherein the medical device produces a same stimulation pulse simultaneously at the first conductor of the first implantable percutaneous medical lead and at the first conductor of the second implantable percutaneous medical lead.

10. The implantable medical system of claim 8, wherein the second implantable percutaneous medical lead further comprises:
a second plurality of distal ring electrodes; and
a second conductor electrically coupled to the stimulation engine, extending through the percutaneous lead body of the second implantable percutaneous medical lead, and electrically coupled to the second plurality of distal ring electrodes of the second implantable percutaneous medical lead.

11. The implantable medical system of claim 5, wherein the implantable percutaneous medical lead is removable from the mechanical coupling to the medical device.

12. A method of providing electrical stimulation therapy across multiple vertebral segments, comprising:
generating an electrical stimulation pulse at a stimulation engine of a medical device;
carrying the electrical stimulation pulse through a first electrical conductor within an implantable percutaneous medical lead that is mechanically coupled to the medical device;
providing the electrical stimulation pulse at a first plurality of distal ring electrodes of the implantable percutaneous medical lead that are electrically coupled to the first electrical conductor wherein the first plurality of distal ring electrodes span the multiple vertebral segments;
receiving the electrical stimulation pulse at a second plurality of distal ring electrodes of the implantable percutaneous medical lead; and
returning the electrical stimulation pulse through a second electrical conductor that is within the implantable percutaneous medical lead and that is electrically coupled to the second plurality of distal ring electrodes, wherein the first plurality of distal ring electrodes and the second plurality of distal ring electrodes are interleaved so that at least one distal ring electrode of the second plurality is located between two distal ring electrodes of the first plurality.

13. The method of claim 12, further comprising:
generating a second electrical stimulation pulse;
carrying the second electrical stimulation pulse through a third electrical conductor within the first implantable percutaneous medical lead; and
providing the second electrical stimulation pulse at a third plurality of distal ring electrodes of the first implantable percutaneous medical lead that are electrically coupled to the third electrical conductor.

14. The method of claim 12, further comprising:
carrying the electrical stimulation pulse through a first electrical conductor within a second implantable percutaneous medical lead; and
providing the electrical stimulation pulse at a first plurality of distal ring electrodes of the second implantable percutaneous medical lead.

15. The method of claim 14, wherein generating a stimulation pulse comprises producing a same stimulation pulse simultaneously at the first conductor of the first implantable percutaneous medical lead and at the first conductor of the second implantable percutaneous medical lead.

16. The method of claim 15, further comprising:
receiving the electrical stimulation pulse at a second plurality of distal ring electrodes of the second implantable percutaneous medical lead; and
returning the electrical stimulation pulse through a second electrical conductor that is within the second implantable percutaneous medical lead and that is electrically coupled to the second plurality of distal ring electrodes of the second implantable percutaneous medical lead.

17. The method of claim 16, wherein the first plurality of distal ring electrodes of the second implantable percutaneous medical lead and the second plurality of distal ring electrodes of the second implantable percutaneous medical lead are interleaved.

* * * * *